US008969272B2

(12) United States Patent
Patil et al.

(10) Patent No.: US 8,969,272 B2
(45) Date of Patent: Mar. 3, 2015

(54) HYDROXYAROMATIC FUNCTIONALIZED POLYALPHA-OLEFINS

(75) Inventors: Abhimanyu Onkar Patil, Westfield, NJ (US); Margaret May-Som Wu, Skillman, NJ (US); Stephen Zushma, Clinton, NJ (US); Anura Abhimanyu Patil, Westfield, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1061 days.

(21) Appl. No.: 12/108,312

(22) Filed: Apr. 23, 2008

(65) Prior Publication Data

US 2009/0270296 A1    Oct. 29, 2009

(51) Int. Cl.
*C09K 15/08*    (2006.01)
*C08K 5/13*    (2006.01)
*C10L 1/16*    (2006.01)
(Continued)

(52) U.S. Cl.
CPC . *C08F 8/00* (2013.01); *C07C 37/14* (2013.01); *C07C 39/06* (2013.01); *C08L 101/00* (2013.01); *C10M 107/30* (2013.01); *C10M 177/00* (2013.01); *C10M 2205/0245* (2013.01); *C10M 2205/0265* (2013.01); *C10M 2205/0285* (2013.01); *C10N 2220/022* (2013.01); *C10N 2220/023* (2013.01); *C10N 2230/02* (2013.01);
(Continued)

(58) Field of Classification Search
CPC ..... C08F 8/00; C08L 101/00; C08L 2666/06; C10M 107/30; C10M 177/00; C10M 2205/0245; C10M 2205/0265; C10M 2205/0285; C10N 2220/022; C10N 2220/023; C10N 2230/02; C10N 2230/08; C10N 2230/10; C10N 2260/06; C07C 37/14; C07C 37/06

USPC .................. 508/110, 584–587, 591; 585/700
See application file for complete search history.

(56) References Cited

U.S. PATENT DOCUMENTS 4,234,435 A    11/1980 Meinhardt et al.
4,871,476 A *  10/1989 Yoshimura et al. ........... 508/505
(Continued)

FOREIGN PATENT DOCUMENTS

EP    0 377 305    7/1990
EP    0377305 A1 *  7/1990
(Continued)

OTHER PUBLICATIONS

Shuikin et al., Catalytic Synthesis of Alkylphenols, Russian Chemical Reviews, Oct. 1960, vol. 29, No. 10, p. 560-576.
(Continued)

*Primary Examiner* — Ellen McAvoy
*Assistant Examiner* — Latosha Hines
(74) *Attorney, Agent, or Firm* — Luke A. Parsons; Catherine L. Bell

(57) ABSTRACT

This invention relates to a hydroxyaromatic functionalized polyalpha-olefin comprising the product of the combination of:
a) a polyalpha-olefin comprising one or more C3 to C20 linear alpha-olefins and having at least 10% vinylidene unsaturation, a viscosity index of 80 to 400, an Mn of 300 to about 20,000, and a pour point of 0° C. or less; and
b) a hydroxyaromatic moiety;
wherein the analine point of the functionalized polyalpha-olefin is at least 10° C. lower than the analine point of the polyalpha-olefin.

37 Claims, 3 Drawing Sheets

(51) Int. Cl.
*C10L 1/18* (2006.01)
*C07C 37/66* (2006.01)
*C08F 8/00* (2006.01)
*C07C 37/14* (2006.01)
*C07C 39/06* (2006.01)
*C08L 101/00* (2006.01)
*C10M 107/30* (2006.01)
*C10M 177/00* (2006.01)

(52) U.S. Cl.
CPC ......... *C10N 2230/08* (2013.01); *C10N 2230/10* (2013.01)
USPC .......... 508/584; 508/585; 508/586; 508/587; 508/591

(56) References Cited

U.S. PATENT DOCUMENTS

| | | | |
|---|---|---|---|
| 5,017,299 A | 5/1991 | Gutierrez et al. | |
| 5,132,478 A * | 7/1992 | Ho et al. | 585/467 |
| 5,186,851 A | 2/1993 | Gutierrez et al. | |
| 5,286,823 A | 2/1994 | Rath | |
| 5,334,775 A | 8/1994 | Gutierrez et al. | |
| 5,496,480 A | 3/1996 | Rollin et al. | |
| 5,498,809 A | 3/1996 | Emert et al. | |
| 6,875,897 B1 | 4/2005 | Lange et al. | |
| 6,914,163 B2 | 7/2005 | Lange et al. | |
| 2008/0146469 A1 * | 6/2008 | Sato et al. | 508/110 |
| 2008/0234157 A1 * | 9/2008 | Yoon et al. | 508/591 |

FOREIGN PATENT DOCUMENTS

| | | |
|---|---|---|
| EP | 0 440 507 | 8/1991 |
| EP | 0 475 391 | 3/1992 |
| EP | 0 462 319 | 12/1994 |
| GB | 1 483 067 | 8/1977 |
| WO | WO 93/24539 | 12/1993 |
| WO | WO 9324539 | * 12/1993 |
| WO | WO 2007/011459 | 1/2007 |
| WO | WO 2007/011462 | 1/2007 |
| WO | WO 2007/011973 | 1/2007 |
| WO | WO 2007/050071 | 5/2007 |

OTHER PUBLICATIONS

Yanjarappa et al., *Synthesis of poly(1-hexene)s end-functionalized with phenols*, Polymer International, Sep. 2005, John Wiley and Sons Ltd GB, 2005, vol. 54, No. 9, pp. 1310-1313.

* cited by examiner

GPC of the phenol functionalized PAO

GPC of the starting PAO

LOG (MW)

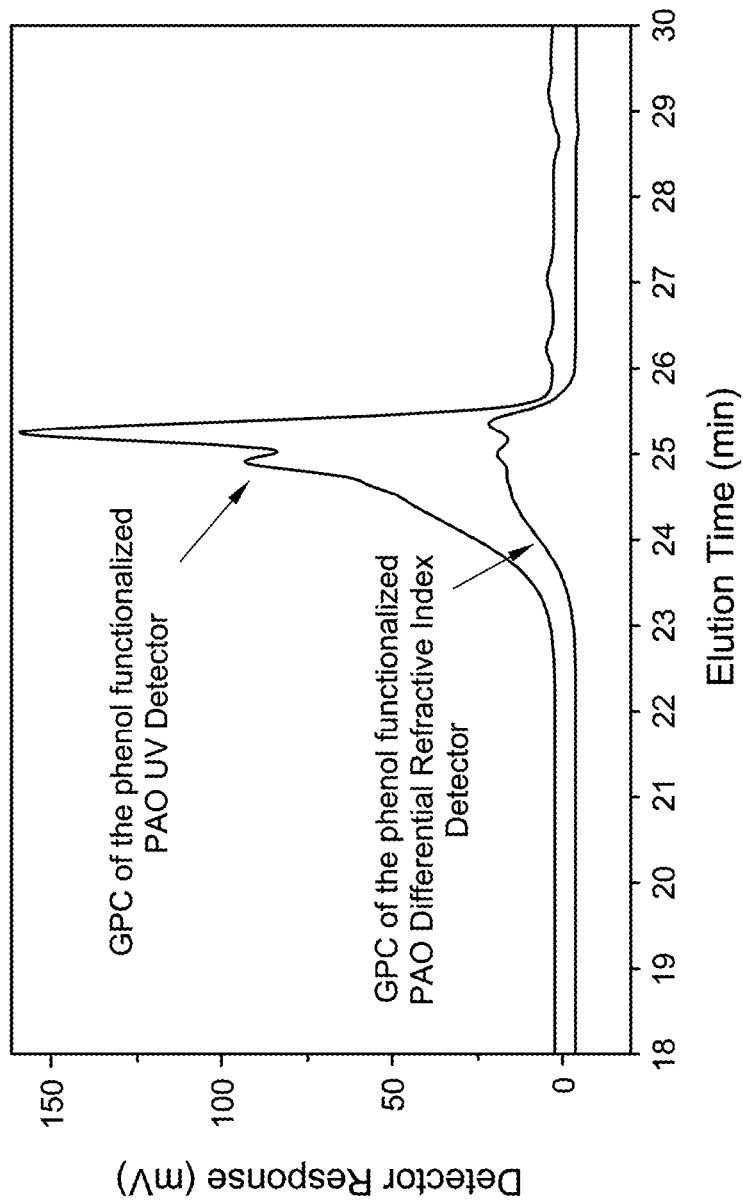

US 8,969,272 B2

HYDROXYAROMATIC FUNCTIONALIZED POLYALPHA-OLEFINS

FIELD OF THE INVENTION

The present disclosure relates to hydroxyaromatic functionalized polyalpha-olefin compositions, processes to manufacture the hydroxyaromatic functionalized polyalpha-olefin compositions and uses of the hydroxyaromatic functionalized polyalpha-olefin compositions. The compositions of the present disclosure are hydroxyaromatic functionalized polyalpha-olefin compositions that are liquids that have improved thermo- and oxidative stability, higher viscosity index and improved cold temperature properties. The processes disclosed herein employ solubilized acid alkylation catalysts.

BACKGROUND OF THE INVENTION

A lubricant is a substance capable of reducing friction, heat and wear when introduced as a film between solid surfaces. Efforts to improve upon the performance of mineral oil based lubricants have been the focus of important research and development activities in the petrochemical industry for over 50 years. Maintenance of friction reducing properties, extended useful life in terms of thermal and oxidative stability and wear protection, improved viscosity index and pour point equal to or better than miner oil are performance areas where research and development activities have occurred. (Viscosity index is a number assigned as a measure of the constancy of the viscosity of a lubricating oil with change of temperature with higher numbers indicating viscosities that change little with temperature, and is determined according to ASTM D2270.) These efforts have led to the introduction of a number of synthetic fluids including polyalpha-olefin (PAO) synthetics primarily made by oligomerization of alpha-olefins or 1-alkenes. A synthetic fluid is a term that can describe materials useful as lubricants, heat transfer agents, and corrosion inhibition among other uses. Polyalpha-olefin synthetic fluid compositions are saturated hydrocarbons and thus are less polar than mineral oil based compositions that can contain polar moieties including aromatics. To improve the solvency and dispersancy of poly alpha-olefin (PAO) type fluids a polar co-basestock is added to the composition to help dissolve polar additives of the composition and sludge during usage. A polar co-basestock such as ester or alkylaromatics is typically used in amounts of about 3 to about 50 weight percent of the basestock composition. The polar co-basestock could introduce undesirable side effects such as hydrolytic instability if an ester co-basestock is used or poorer low temperature properties, reduced cleanliness properties if typical alkylaromatic co-basestocks are used. Thus, synthetic fluids are often formulated with additives to enhance their properties for specific applications. Additives that are commonly used can include oxidation inhibitors, dispersants, detergents, rust inhibitors, antiwear agents, extreme pressure agents, metal passivators, pour point depressants, viscosity index (VI) improvers, and the like. Thus formulated fluids are compositions comprising a number of components, the largest volume component being the fluid basestock. Adding to the complexity of formulating lubricating oils is the trend to ever-higher oil performance standards dictated by the increasing complexity of newer equipment and engines. There is a continuing need to improve the suite of properties of the fluid basestock to provide improved performance of the formulated fluid in all areas required including thermal and oxidative stability.

Aromatic hydroxy compounds can be alkylated with polyolefins using acid catalysts for the preparation of polyalkenylphenols. This Friedel-Crafts alkylation does not generally lead to pure monoalkylation products since the alkylated products are more reactive than the unsubstituted starting materials. A mixture of different mono-, di- and polyalkylation products is therefore generally formed. Moreover, when high molecular weight alkylating agents are used, fragmentation reactions frequently occur both in the polyolefin and in the alkylated product, so that as a rule a product mixture having a complex composition is obtained. (For more information on alkylation of Phenols see Shuikin, N. I.; Viktorova, E. A., Russ. Chem. Rev. 29,560 (1960) and U.S. Pat. No. 5,334,775.)

Such mixtures are unsuitable for many industrial applications. Rather, products of defined composition are required, frequently monoalkylation products, it also being possible for the position of the alkylation to be relevant.

Prior to this invention, known processes for the alkylation of hydroxyaromatic compounds with polyolefins have had at least one or more of the following disadvantages: 1) large excesses of hydroxyaromatic compound and/or amounts of catalyst are required, 2) the polyolefin used must contain a high proportion of alpha-olefin terminal units, 3) fragmentation reactions of the polyolefin or of the alkylated product take place, 4) undesirable byproducts, such as polyalkylation products or products alkylated in an undesirable position, are also obtained, and/or 5) the reaction times are long.

PAOs are non-polar and hence it is desirable to increase their polarity via alkylation with polar molecules such as phenols. PAOs produced using metallocene type catalysts have high amounts of terminal vinylidene type double bond or double bonds at more accessible positions. Thus, they are more reactive towards alkylation with hydroxyaromatic compounds like phenols or naphthols.

Therefore, a need exists for polyalkenylhydroxyaromatics and a process to prepare them that address one or more of the aforementioned disadvantages.

SUMMARY OF THE INVENTION

This invention relates to a hydroxyaromatic functionalized polyalpha-olefin comprising the product of the combination of:

a) a polyalpha-olefin comprising one or more C3 to C20 linear alpha-olefins and having at least 10% vinylidene unsaturation, a viscosity index of 80 to 400, an Mn of 300 to about 20,000, and a pour point of 0° C. or less; and b) a hydroxyaromatic moiety;

wherein the analine point of the functionalized polyalpha-olefin is at least 10° C. lower than the analine point of the polyalpha-olefin.

BRIEF DESCRIPTION OF THE FIGURES

FIG. 4 provides a GPC DRI/UV 254 plot of the phenol reacted PAO based on polystyrene calibration.

DETAILED DESCRIPTION

Figure 1:
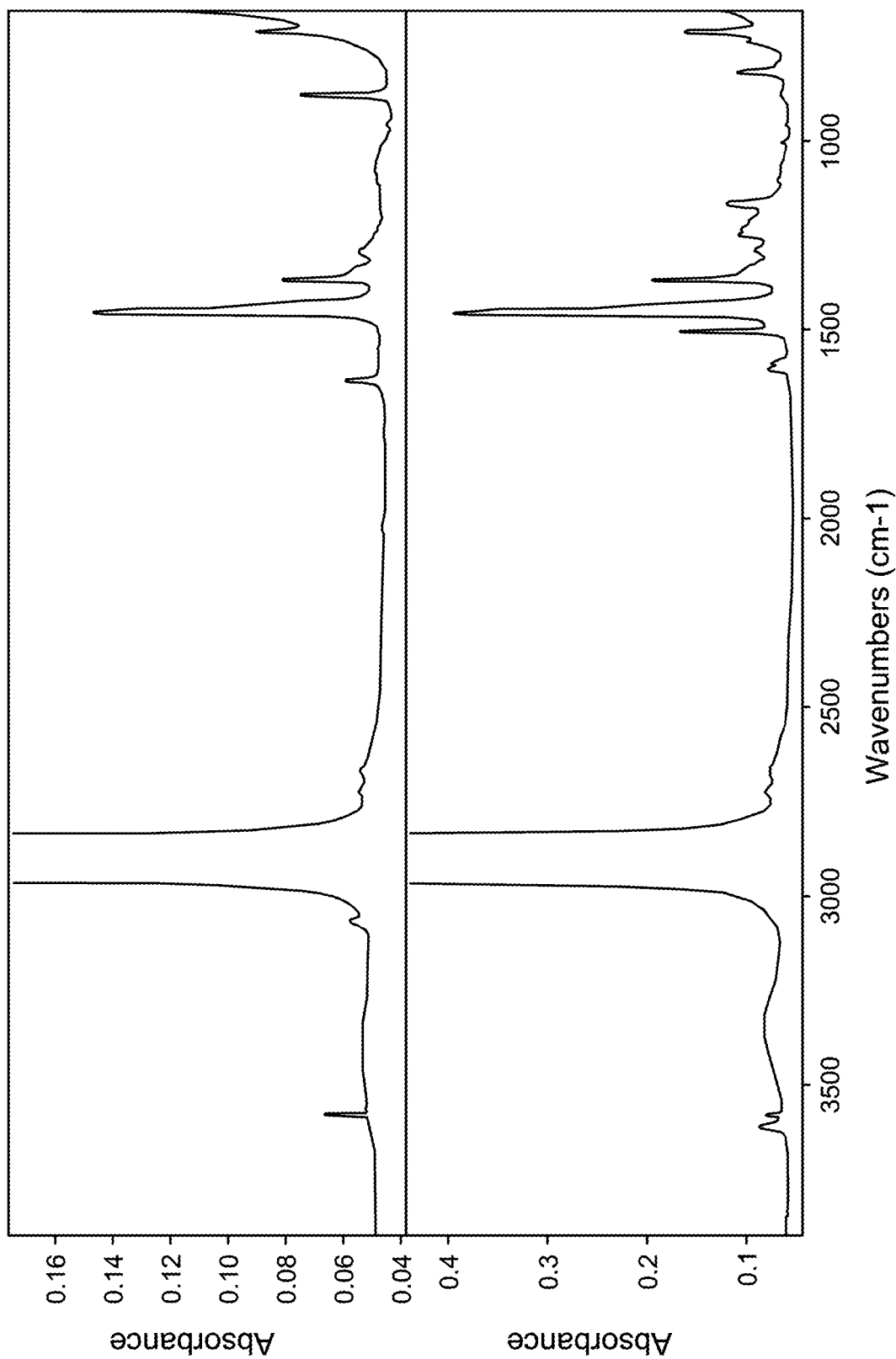
FIG. 1 is an FTIR Spectra of the starting PAO (top spectrum) and the phenol reacted PAO (bottom spectrum).
Figure 2:
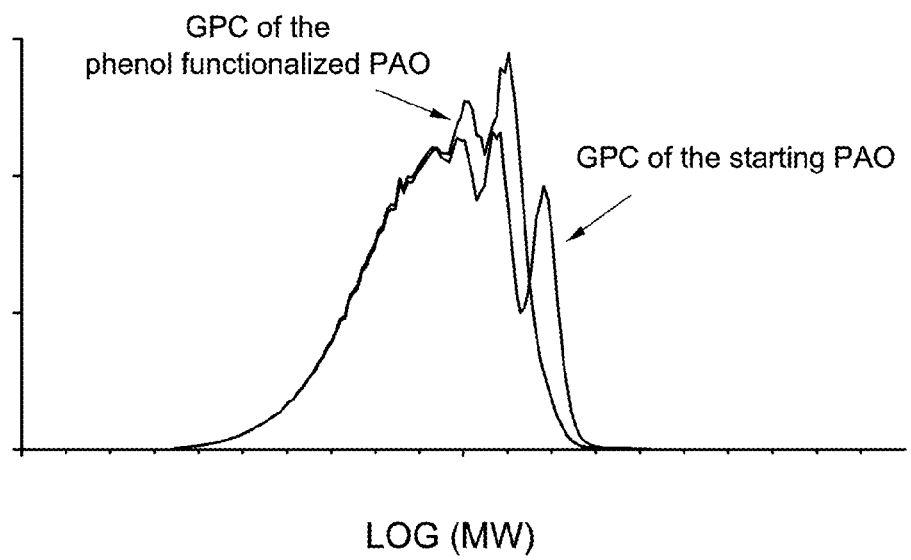
FIG. 2 provides a GPC of the starting PAO and the phenol functionalized PAO based on polystyrene calibration.
Figure 3:
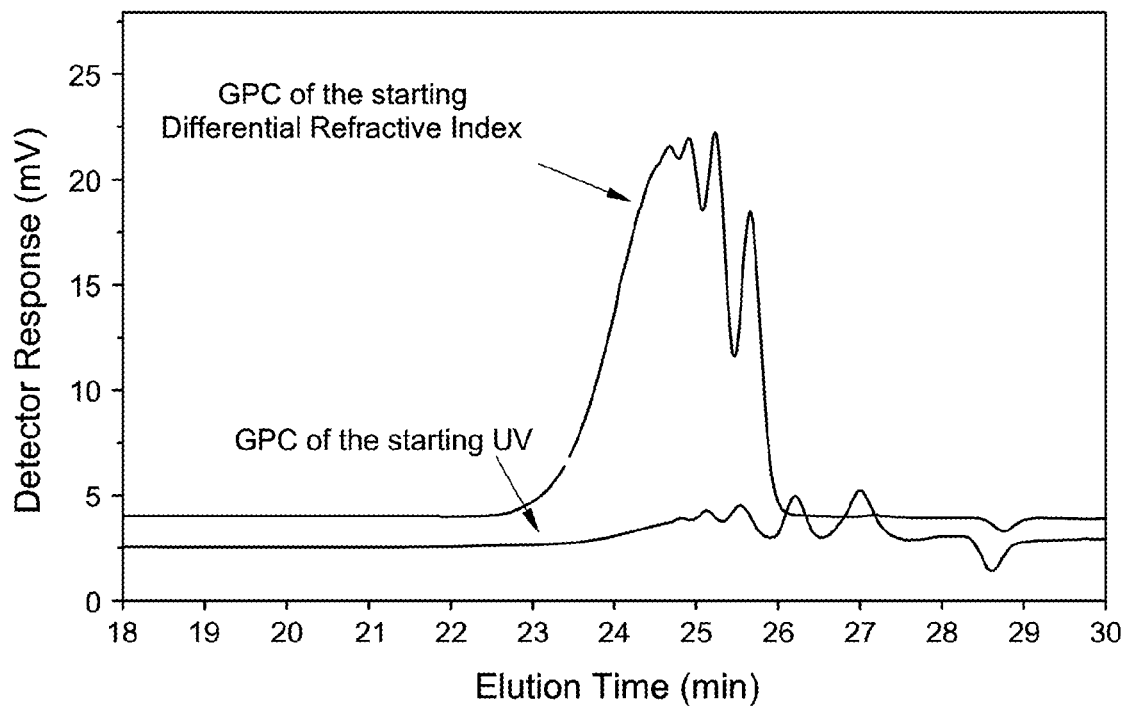
FIG. 3 provides a GPC DRI/UV 254 plot of the starting PAO based on polystyrene calibration.

The present invention provides a functionalized polyalpha-olefin composition comprising a hydroxyaromatic moiety and a polyalpha-olefin (PAO), wherein the hydroxyaromatic functionalized polyalpha-olefin (HAFPAO) has improved oxidative and/or improved polarity/solvency properties when compared to unfunctionalized PAOs. In one aspect, the PAO utilized in the HAFPAO is produced by metallocene based polymerization, providing a hydroxyaromatic functionalized metallocene-derived PAO (HAFMPAO). PAO's produced under metallocene conditions have unique physical properties, typically including having more terminal vinylidene groups or more accessible olefinic unsaturation, in contrast to PAO's produced by other polymerization processes, especially the Lewis Acid catalyzed polymerization, that include various types of unsaturation sites.

In particular, the HAFPAOs of the invention are monofunctionalized with a hydroxyaromatic moiety. In a preferred embodiment at least 90 wt. % of the HAFPAOs are monofunctionalized, preferably at least 95 wt. %, preferably at least 99 wt. %, preferably at least 100 wt. %, based upon the weight of the HAFPAO.

In another aspect, it is generally more desirable to have lesser amounts of olefin group remaining in the alkylated product. Usually, the HAFPAOs of the invention have less than 30%, or more preferably less than 15%, or more preferably less than 5%, in particular preferably less than 2%, even more particular less than 1% (e.g., about 0.5% or less) remaining sites of unsaturation after alkylation based on starting material. The degree of alkylation or the amount of remaining olefins can be controlled by the stoichiometric ratio of hydroxyaromatic compound to olefins present in the reaction process. A molar excess of alkylating compound will effect more efficient alkylation of the PAO, such that less than 30%, or more preferably less than 15%, or more preferably less than 5%, in particular preferably less than 2%, even more particular less than 1% of unsaturation remain after alkylation, based on starting material. If a lesser amount of alkylating agent is utilized, the degree of alkylation can be controlled, such that virtually all of the alkylating agent is incorporated into the PAO.

The polarity of a lubricant base stock is measured by aniline point method, as described in ASTM Method D611. Usually, higher aniline point means low polarity and lower aniline point means higher polarity and higher dispersancy for base stock. Lubricant base stock. HAF-PAO (and HADMFPAO) compounds prepared herein preferably have an aniline point of at least 5° C. less than the PAO (as measured on the PAO prior to any combination with the hydroxyaromatic moiety), preferably 10° C. less or preferably 12° C. or less, preferably 15° C. or less, preferably 18° C. or less, preferably 20° C. or less, preferably 25° C. or less, preferably 30° C. or less, preferably 35° C. or less. Typically, the unfunctionalized PAO or metallocene-based PAO have aniline point range from 110° C. to 170° C., depending on fluid viscosity. For example, the current commercial PAO produced from oligomerization of large linear alpha-olefin of C8 to C14 by either $BF_3$ or $AlCl_3$ type catalysts will have an aniline point vs. 100° C. kinematic viscosity in cS according to the following equation:

$$\text{Aniline Point of PAO in } °C. = 16.016 \times Ln(100° C. \text{ kinematic viscosity in cS}) + 97.964.$$

The metallocene based PAOs have similar aniline point range. The HAFMPAO compounds prepared herein preferably have an aniline point of least 5° C. less than the starting metallocene-based PAO (as measured on the PAO prior to any combination with the hydroxyaromatic moiety), preferably 10° C. less or preferably 12° C. or less, preferably 15° C. or less, preferably 18° C. or less, preferably 20° C. or less, preferably 25° C. or less, preferably 30° C. or less, preferably 35° C. or less.

HAF-PAO (and HAFMPAO) compounds prepared herein preferably have a 100° C. Kinematic viscosity (as measured by ASTM D445 at 100° C.) of 3 to 1000 cSt, alternately from 5 to 800 cSt, alternately from 10 to 750 cSt, alternately from 15 to 500 cSt.

HAF-PAO (and HAFMPAO) compounds prepared herein preferably have a Kinematic viscosity (as measured by ASTM D445 at 40° C.) of 6 to 30,000 cSt, alternately from 8 to 15,000 cSt, alternately from 15 to 10,000 cSt, alternately from 6 to 5,000 cSt.

In another preferred embodiment, HAF-PAO (and HAFM-PAO) compounds prepared herein have a viscosity index (VI) of 80 to 400 preferably 90 to 350, preferably 100 to 300, as measured by ASTM D2270.

In another preferred embodiment, HAF-PAO (and HAFM-PAO) compounds prepared herein have a pour point of –0° C. or less preferably –5° C. or less, more preferably –10° C. or less, most preferably –15° C. or less, as determined by ASTM D97, or equivalent methods.

In another preferred embodiment, HAF-PAO (and HAFM-PAO) compounds prepared have a kinematic viscosity at 100° C. of at 3 cSt to 1000 cSt (as measured by ASTM D445); a viscosity index of at least 80-400 (as determined by ASTM D2270); a pour point of –0° C. or less (as determined by ASTM D97 or equivalent methods).

Lubricant oxidative stability is an important property. This oxidative stability can be measured by many methods as described in ASTM D2272 method or ASTM D2893 method, or some modified version of these methods. One method to evaluate the oxidative stability is by measuring the induction temperature by differential scanning calorimetry (DSC). In this method, an oil sample in a DSC was heated under 100 psi air at 10° C./minute heating rate, from room temperature to 400° C. The temperature when a dramatic increase in heat release is defined as the oxidation induction temperature. Usually, higher induction temperature means higher oxidative stability—a desirable property. HAF-PAO (and HAFM-PAO) compounds prepared herein preferably have an oxidation induction temperature of 195° C. or more, preferably 200° C. or more, preferably 225° C. or more preferably 245° C. or more, preferably 250° C. or more, preferably 255° C. or more. HAF-PAO (and HAFMPAO) compounds prepared herein preferably have an oxidation induction temperature of at least 5° C. higher than the PAO (as measured on the PAO prior to any combination with the hydroxyaromatic moiety), preferably 10° C. or more, preferably 15° C. or more, preferably 20° C. or more, preferably 30° C. or more, preferably 40° C. or more, preferably 50° C. or more, preferably 60° C. or more, preferably 80° C. or more, preferably 100° C. or more.

The present disclosure also includes a process for the preparation for the preparation of a hydroxyaromatic functionalized polyalpha-olefin compound comprising: contacting at least one hydroxyaromatic compound and at least one polyalpha-olefin (preferably metallocene-derived) in the presence of an acidic alkylation catalyst under alkylation conditions. The process optionally includes separating and recovering the alkylaromatic compound.

Suitable catalysts useful for the hydroxyalkylation reaction include, but are not limited to, Lewis acids and protonic acids (Bronsted acids), such as sulfuric acid, hydrochloric acid, phosphoric acid, etc. as well as Amberlyst 15 (styrene-divinylbenzene polymer, Rohm & Haas, Co.) or suitable solid acid catalysts, such as zeolites (MCM22, ZMS-48, etc), acid clays, or amorphous solid acid catalysts (WOx/ZrO$_2$, silica-aluminate, etc.).

These and other features and attributes of the disclosed hydroxyaromatic functionalized polyalpha-olefin compositions suitable as liquid lubricant compositions or additives and processes for the preparation of the hydroxyaromatic functionalized polyalpha-olefin compositions of the present disclosure and their advantageous applications and/or uses will be apparent from the detailed description which follows.

Advantageously, the hydroxyaromatic moiety include, but are not limited to, monohydric phenols such as phenol, o-, m-, or p-cresol, o-, m-, or p-ethylphenol, o-, m-, or p-isopropylphenol, o-, m-, or p-tert-butylphenol, o-, m-, or p-sec-butylphenol, 4-tert-butyl-6-methylphenol, 2,4-dimethylphenol, 2-methyl-4-ethylphenol, 2,4-diisopropylphenol, 4-methyl-6-iso-propylphenol, 2,6-di-tert-butylphenol, 2-tert-butyl-4-methylphenol, 3-methyl-6-tert-butylphenol, 2-chloro-4-methylphenol, p-chlorophenol, p-bromophenol, 2,4-dichlorophenol, 2,4-dibromophenol, 2-methyl-4-chlorophenol, 2-methyl-4-bromophenol, 2,4-dichloro-3-methylphenol, 3-methyl-6-cyclohexylphenol, 3-methyl-4-cyclohexylphenol, and so forth; dihydroxyaromatics such as resorcinol, hydroquinone, catechol, 2-methylresorcinol, 2-chlororesorcinol, 2-carboxyresorcinol, 2-chlorohydroquinone, 4-tert-butylresorcinol, and so forth; trihydroxyaromatics such as pyrogallol, phloroglucinol, 1,2,4-trihydroxybenzene, gallic acid and so forth; naphthols such as alpha-naphthol, beta-naphthol, 2-hydroxy-3-carboxy naphthalene, 1-hydroxy-5-methyl naphthalene, 2-hydroxy-5-methyl naphthalene, 2-hydroxy-8-isopropyl-naphthalene, 2-hydroxy-5-isopropyl naphthalene, and so forth; and anthranols and so forth.

Generally, all that is required of a hydroxyaromatic for the purposes of this invention is that there be at least one aromatic ring bound to a hydroxyl group and having at least one open carbon (e.g. bound to a hydrogen) at a position ortho or para thereto.

Polymer alkylating agents which are useful in the present invention are polymers containing at least one carbon-carbon double bond (olefinic, or "ethylenic") unsaturation and which are not so sterically hindered, or in reactive competition with other functional groups, so as to render them unable to participate in the catalytic alkylation of the chosen hydroxyaromatic compound. As long as a chosen double bond will react in the presence of a chosen catalyst so as to alkylate a chosen hydroxyaromatic compound, such a bond will be deemed a "reactive" unsaturation and the polymer possessing such an unsaturation will be deemed a polymer alkylating agent.

Generally, terminal vinyl or vinylidene double bonds are most suitable for functionlization by hydroxyaromatic moieties. PAOs generated by metallocene polymerization provide useful polymers that can be alkylated with hydroxyaromatic compounds as the metallocene derived PAOs enjoy having the olefinic portion of the molecule that is in the readily accessible part of the polymer.

Useful polymers in the present invention include polyalkenes including homopolymer, copolymer (used interchangeably with interpolymer) and mixtures thereof. Homopolymers and interpolymers include those derived from polymerizable olefin monomers of 2 to about 16 carbon atoms; usually 6 to about 16 carbon atoms, or 6 to 14 carbon atoms.

The interpolymers are those in which two or more olefin monomers are interpolymerized according to well-known conventional procedures to form polyalkenes having units within their structure derived from each of said two or more olefin monomers. Thus, "interpolymer(s)" as used herein is inclusive of copolymers, terpolymers, tetrapolymers, and the like.

Useful polymers include those described in U.S. Pat. Nos. 4,234,435, 5,017,299, 5,186,851 and European Patent No. 0 462 319-A1. Particular reference is made to the alpha-olefin polymers to be made using organometallic coordination compounds as disclosed therein. Examples of these polymers are described in WO 2007/011973, WO 2007/011459, WO 2007/011462, and WO 2007/011462. Further useful polymers include ethylene/alpha-olefin copolymers such as those disclosed in U.S. Pat. Nos. 5,017,299 and 5,186,851.

The active polymers for use in this invention possess at least one carbon-carbon unsaturated double bond. The unsaturation can be terminal, internal, or both. Preferred polymers have terminal unsaturation, such as those PAOs prepared by metallocene polymerization processes. For the purposes of this invention, "terminal unsaturation" refers to the unsaturation provided by the last monomer unit located in the polymer. The unsaturation can be located anywhere in this terminal monomer unit. Terminal olefinic groups include ethenylidene (also known as "vinylidene") unsaturation, $R^aR^bC=CH_2$; trisubstituted olefin unsaturation, $R^aR^bC=CRCH$; vinyl unsaturation, $R^aHC=CH_2$; 1,2-disubstituted terminal unsaturation, $R^aHC=CHR^b$; and tetra-substituted terminal unsaturation, $R^aR^bC=CR^cR^d$. At least one of $R^a$ and $R^b$ is a polymeric group, and the remainder are hydrocarbyl groups, polymeric or otherwise, the same or different.

The homopolymers, copolymers and interpolymers of the present invention can be conveniently characterized based on molecular weight range. In particular and advantageously, polymers and copolymers of "low" molecular weights are useful herein. Low molecular weight polymers are considered to be polymers having a number average molecular weight of less than 20,000, preferably from about 224 to about 20,000, more preferably from about 300 to about 18,000, more preferably from about 500 to about 15,000, more preferably from 750 to 10,000, more preferably 1000 to 8,000, more preferably 1000 to 7,500, more preferably 1,500 to 5,000. The low molecular weights are number average molecular weights measured by gel permeation chromatography (GPC). Low molecular weight polymers are useful in forming dispersants for fuel and lubricant additives. In particular, the HAFMPAOs of the invention have low molecular weights, and therefore have molecular weight ranges of between about 224 and about 20,000, more particularly between about 400 and about 10,000 and more particularly between about 420 and about 5000.

The values of the ratio Mw/Mn, also referred to as molecular weight distribution, (MWD) are typically from more than 1 to 20, alternately from greater than 1 to 4, alternately from about 1.1 to about 3.0.

Useful olefin monomers from which the PAO's can be derived are polymerizable olefin monomers characterized by the presence of one or more unsaturated double bonds (i.e., $>C=C<$); that is, they are monoolefinic monomers such as propylene, butene-1, octene-1, decene-1, dodecene, tetradecene, hexadecene, and the like.

The alpha-olefins used to make PAOs useful herein include, but are not limited to, C3 to C24 alpha-olefins, preferably C4 to C20 alpha-olefins, such as propylene, 1-butene, 1-pentene, 1-hexene, 1-heptene, 1-octene, 1-nonene, 1-decene, 1-undecene, 1-dodecene, 1-tridecene and 1-tetradecene being preferred. Useful PAO's are preferably oligomers or polymers with carbon numbers starting from C20 and higher made from C3 to C20 alpha-olefins in one embodiment, and oligomers or polymers with carbon number starting from C24 and higher made from C3 to C14 alpha-olefins in another embodiment. In one embodiment, the olefin is propylene, and the polymer product is a mixture of pentamer and higher oligomers or polymers of propylene. In another embodiment, the olefin is 1-butene, and the PAO is a mixture of pentamers and higher oligomers of 1-butenes. In another embodiment, the olefin is 1-pentene, and the PAO is a mixture of tetramers and pentamers and higher of 1-pentene. In another embodiment, the olefin is 1-hexene, and the PAO is a mixture of tetramers and pentamers (and higher) of 1-hexene. In another embodiment, the olefin is 1-heptene, and the PAO is a mixture of trimers and tetramers and higher of 1-heptene. In another embodiment, the olefin is 1-octene, and the PAO is a mixture of trimers and tetramers and higher of 1-octene. In another embodiment, the olefin is 1-nonene, and the PAO is a mixture of trimers and tetramers and higher of 1-nonene. In another embodiment, the olefin is 1-decene, and the PAO is a mixture of dimer, trimers and tetramers and higher of 1-decene. In another embodiment, the olefin is 1-undecene, and the PAO is a mixture of trimers and tetramers and higher of 1-undecene. In another embodiment, the olefin is 1-dodecene, and the PAO is a mixture of dimer and trimers and higher of 1-dodecene.

In a preferred embodiment, the PAO comprises two or more monomers, alternatively three or more monomers, alternatively four or more monomers, and alternatively five or more monomers, alternatively six or more monomers (preferably C3 to C20 alpha-olefins). For example, a C3, C4, C6, C12-alpha-olefin mixture, a C3, C12-alpha-olefin mixture, a C3, C12, C14-alpha-olefin mixture, a C4, C12-alpha-olefin mixture, a C4, C12, C14-alpha-olefin mixture, a C4, C14-alpha-olefin mixture, a C6, C12-alpha-olefin mixture, a C6, C12, C14-alpha-olefin mixture, a C5, C12, C14-alpha-olefin mixture, a C6, C10, C14-alpha-olefin mixture, a C6, C8, C12-alpha-olefin mixture, a C8, C10, C12-linear alpha-olefin mixture, or a C6, C7, C8, C9, C10, C11, C12, C13, C14-linear alpha-olefin mixture, or a C4, C6, C8, C10, C12, C14, C16, C18-linear alpha-olefin mixture can be used as a feed. In a preferred embodiment, the PAO is a co-oligomer or copolymer of C6, C12, C10, C14 alpha-olefin monomers. In particularly preferred embodiments, the PAO comprises a mixture of C6, C10, and C12 alpha-olefin monomers, alternately C6, C12, and C14 alpha-olefin monomers, alternately C6, C8, C10 and C12 alpha-olefin monomers. In a preferred embodiment the PAO is prepared form a C4 raffinate stream.

In an alternate embodiment, ethylene is present in the PAO at from 0 wt. % to 5 wt. %, preferably at 0 wt. %. In an alternate embodiment, propylene is present in the PAO at from 0 wt. % to 5 wt. %, preferably at 0 wt. %. In an alternate embodiment, isobutylene is present in the PAO at from 0 wt. % to 5 wt. %, preferably at 0 wt. %. In an alternate embodiment, n-butene is present in the PAO at from 0 wt. % to 5 wt. %, preferably at 0 wt. %.

In an alternate embodiment, the PAO comprises at least 50 wt. % (preferably at least 60 wt. %, preferably at least 75 wt. %, based upon the weight of the PAO) of a C6 or greater linear alpha-olefin, preferably a C8 or greater alpha-olefin, preferably a C10 or greater alpha olefin.

In another embodiment, the PAO's produced directly from the oligomerization or polymerization process are unsaturated olefins. The amount of unsaturation can be quantitatively measured by bromine number measurement according to ASTM D1159 method or equivalent method, or proton or carbon-13 NMR. Proton NMR spectroscopic analysis can also differentiate and quantify the types of olefinic unsaturation: vinylidene, 1,2-disubstituted, trisubstituted, or vinyl.

Proton NMR spectroscopy can also quantify the extent of short chain branching (SCB) in the olefin oligomer, although carbon-13 NMR can provide greater specificity with respect to branch lengths. In the proton spectrum, the SCB branch methyl resonances fall in the 1.05-0.7 ppm range. SCBs of sufficiently different length will give methyl peaks that are distinct enough to be integrated separately or deconvoluted to provide a branch length distribution. The remaining methylene and methine signals resonate in the 3.0-1.05 ppm range. In order to relate the integrals to CH, $CH_2$, and $CH_3$ concentrations, each integral must be corrected for the proton multiplicity. The methyl integral is divided by three to derive the number of methyl groups; the remaining aliphatic integral is assumed to comprise one CH signal for each methyl group, with the remaining integral as $CH_2$ signal. The ratio of $CH_3/(CH+CH_2+CH_3)$ gives the methyl group concentration.

Similar logic applies to the carbon-13 NMR analysis, with the exception that no proton multiplicity corrections need be made. Furthermore, the enhanced spectral/structural resolution of $^{13}C$ NMR vis a vis $^1H$ NMR allows differentiation of ions according to branch lengths. Typically, the methyl resonances can be integrated separately to give branch concentrations for methyls (20.5-15 ppm), propyls (15-14.3 ppm), butyl-and-longer branches (14.3-13.9 ppm), and ethyls (13.9-7 ppm).

Olefin analysis is readily performed by proton NMR, with the olefinic signal between 5.9 and 4.7 ppm subdivided according to the alkyl substitution pattern of the olefin. Vinyl group CH protons resonate between 5.9-5.7 ppm, and the vinyl $CH_2$ protons between 5.3 and 4.85 ppm. 1,2-disubstituted olefinic protons resonate in the 5.5-5.3 ppm range. The trisubstituted olefin peaks overlap the vinyl $CH_2$ peaks in the 5.3-4.85 ppm region; the vinyl contributions to this region are removed by subtraction based on twice the vinyl CH integral. The 1,1-disubstituted—or vinylidene—olefins resonate in the 4.85-4.6 ppm region. The olefinic resonances, once corrected for the proton multiplicities can be normalized to give a mole-percentage olefin distribution, or compared to the multiplicity-corrected aliphatic region (as was described above for the methyl analysis) to give fractional concentrations (e.g. olefins per 100 carbons).

Generally, the amount of unsaturation strongly depends on the fluid viscosity or fluid molecular weight. Lower viscosity fluid has higher degree of unsaturation and higher bromine number. Higher viscosity fluid has lower degree of unsaturation and lower bromine number. If a large amount of hydrogen or high hydrogen pressure is applied during the polymerization step, the bromine number maybe lower than without the hydrogen presence. Typically, for greater than 20 to 5000 cSt polyalpha-olefin produced from 1-decene or other LAOs in this inventive process, the as-synthesized PAO will have bromine number of from 25 to less than 1, depending on fluid viscosity.

The types of olefinic unsaturations in the PAO fluids produced herein are unique, as confirmed by $^1H$ and $^{13}C$-NMR. They contain a very high amount of vinylidene olefins, $CH_2=CR^1R^2$, and much less of the other types of unsaturation, including trisubstituted or di-substituted olefins.

In an alternate embodiment, vinylidene content of polyalphaolefins made using metallocenes and non-coordination anion activators is higher than the vinylidene content of poly-alpha-olefins produced with metallocenes and methylalumoxane activators. However, the polyalphaolefins made from metallocene and methylalumoxane activators are also useful herein because their double bonds are still in the easily accessible part of the PAO fluid.

A higher amount of vinylidene unsaturation is usually more desirable because this type of olefin is much more reactive for further hydrogenation or for further functionalization such as with hydroxyaromatics. There are many methods described to maximize the amount of vinylidene olefins, such as those disclosed in U.S. Pat. No. 5,286,823. Vinylidene olefins are much more readily hydrogenated or functionalized as disclosed herein to give fully saturated hydrocarbons for high performance base stocks. Usually, the degree of functionalization affects the oxidative stability of the fluid. Fluids with a higher degree of functionalization, and concomitantly lower bromine number, usually have better oxidative stability. The PAOs used in the present invention have high vinylidene content and are therefore more amenable to functionalization, to provide the formation of low bromine number fluids. The bromine number after functionalization is preferably less than 5, more preferably less than 3, more preferably less than 2, more preferably less than 1, more preferably less than 0.5, more preferably less than 0.1. Generally, the lower the bromine number, the better the oxidative stability.

In a preferred embodiment, the PAO's useful herein have at least 10 wt. % vinylidene unsaturation (as measured by proton NMR as described herein), preferably at least 12 wt. %, preferably at least 14 wt. %, preferably at least 15 wt. %, preferably at least 17 wt. %, preferably at least 20 wt. %, preferably at least 22 wt. %, preferably at least 25 wt. % vinylidene unsaturation, based upon the total amount of unsaturations.

In another preferred embodiment, the PAO's useful herein have a viscosity index (VI) of 8- to 400 preferably 90 to 350, preferably 100 to 300, as measured by ASTM D2270.

In another preferred embodiment, the PAO's useful herein have a pour point of $-0°$ C. or less (preferably $-5°$ C. or less, more preferably $-10°$ C. or less, most preferably $-15°$ C. or less, as determined by ASTM D97).

In another preferred embodiment, the PAO's useful herein have a specific gravity (15.6/15.6° C.) of 0.86 or less (preferably 0.855 or less, more preferably 0.85 or less, most preferably 0.84 or less, as determined by ASTM D 4052).

In another embodiment, PAOs useful herein have a kinematic viscosity at 100° C. of at 3 cSt to 1000 cSt (as measured by ASTM D445); a viscosity index of at least 80-400 (as determined by ASTM D2270); a pour point of $-0°$ C. or less (as determined by ASTM D97); and a specific gravity (15.6/15.6° C.) of 0.86 or less (as determined by ASTM D 4052).

Preparing PAOs as described above which meet the various criteria for Mn and Mw/Mn is within the skill of the art and does not comprise part of the present invention. For example, see WO 2007/011973, WO 2007/011459, WO 2007/011462, and WO 2007/011462.

The general process according to the present disclosure is referred to below:

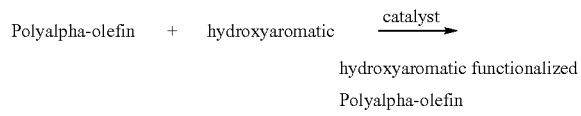

or, more specifically,

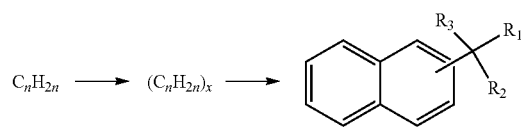

where n is 2 to 20, x is 2 to 1000, R1, R2 and R3 are, independently, hydrogen or a $C_1$ to $C_{2000}$ hydrocarbyl group.

Acidic catalysts capable of effecting alkylation of aromatics with olefins include acidic halides (Lewis acids), protonic acids (Bronsted acids), cation exchange resins, Friedel Crafts catalysts, and solid acids such as Amberlyst 15 (styrene-divinylbenzene polymer, Rohm & Haas, Co.) or Dowex 50W type strongly acidic ion-exchange resins. Exemplary Lewis acids include aluminum chloride, aluminum bromide, iron (III) chloride, zinc chloride, boron trifluoride, their promoted versions, and many others. Exemplary Bronsted acids include sulfuric acid, nitric acid, hydrochloric acid, hydrofluoric acid, phosphoric acid and others. To be effective a catalyst must selectively enable the desired reaction under useful conditions of time and temperature in a useful reaction zone.

Lewis acid alkylation catalysts are understood as meaning both individual acceptor atoms and acceptor atom-ligand complexes, molecules, etc., provided that they have overall (external) Lewis acid (electron acceptor) properties. Such catalysts include halides of boron, aluminum, tin or a transition metal, preferably titanium and iron ($SnCl_4$, $TiCl_4$ and $FeCl_3$). $BF_3$ is particularly preferred.

In an advantageous embodiment, the alkylation catalysts (Lewis acids) are used together with at least one ether as a cocatalyst. The molecular weight of the ethers is generally from 102 to 242 g/mol. $BF_3$ is easy to handle as an etherate complex.

Ethers having a molecular weight of less than 102 g/mol are, for example, dimethyl ether, ethyl methyl ether and diethyl ether. Ethers are selected from symmetrical and asymmetrical ethers which have two hydrocarbon radicals of 6 to 16 carbon atoms in total. These hydrocarbon radicals may be aliphatic, cycloaliphatic or aromatic radicals. Cyclic ethers in which the ether group is part of the ring are also suitable. $Di(C_3-C_8)$alkyl ethers, such as di-n-propyl ether, diisopropyl ether, methyl tert-butyl ether and isopropyl tert-butyl ether, tetrahydrofuran, $di(C_5-C_8)$cycloalkyl ethers, such as dicyclohexyl ether and ethers having at least one aromatic hydrocarbon radical, such as anisole, are included.

Many solid acidic catalysts are also suitable for this alkylation reaction. Examples are large pore zeolites, molecular sieves with strong acidity, natural or synthetic acid clays, solid tungsten oxide on zirconia, solid silica-alumina, or silicoaluminates, etc.

The selected polymer and hydroxyaromatic compound are contacted in the presence of a catalytically effective amount of at least one catalyst under conditions effective to alkylate the aromatic group of the hydroxyaromatic compound.

In a preferred embodiment the residence time for the reaction is 48 hours or less, preferably 36 hours or less, preferably 24 hours or less.

It is known that in the presence of a sufficiently strong acid catalyst, olefins can undergo skeletal rearrangement leading to tertiary carbocations ($R_3C+$, where R=alkyl) and that tertiary carbocations will alkylate aromatic substrates to produce a composition with a quaternary carbon (quaternary benzylic carbon) adjacent to the aromatic ring. One of the advantages of the present disclosure is that hydroxyaromatic functionalized polyalpha-olefin compositions provide thermal and oxidative stability to the composition. An illustrative example of a hydroxyaromatic functionalized polyalpha-olefin composition from the present disclosure having thermal and/or oxidative stability is a composition having more than 20% of the benzylic carbon atoms present as quaternary carbon atoms, preferably more than 25%, preferably more than 30%, as measured by $^{13}$CNMR.

Scheme I (below) is illustrative of the invention, demonstrating the production of a HAFMPAO from metallocene-derived poly-1-decene and phenol, in the presence of a catalyst. The HAFMPAO has primarily only benzylic carbon atoms as quaternary.

Scheme I

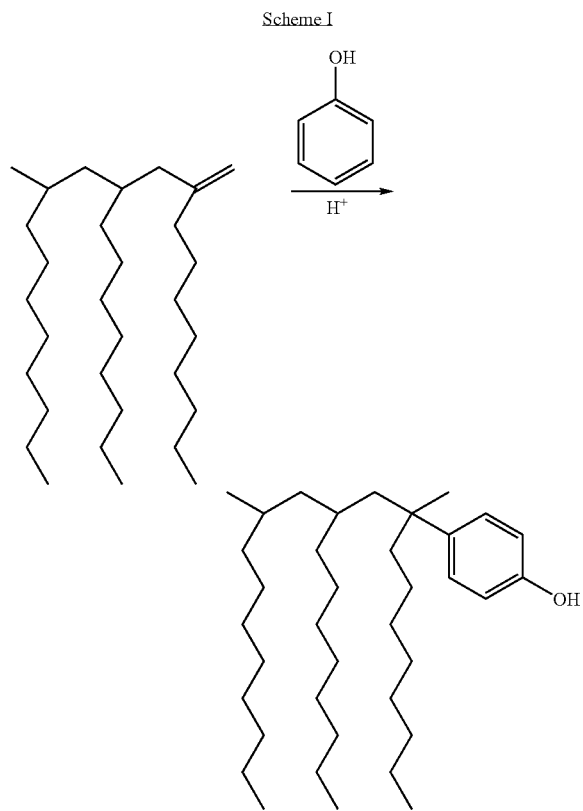

The greater the thermal and oxidative stability of the hydroxyaromatic PAO liquid lubricant composition the lower the requirement for additives to provide required thermal and oxidative stability of the finished lubricant or functional products.

The hydroxyaromatic compound and polymer (PAO) will be typically contacted in a molar ratio of from about 2 to about 0.1, preferably from about 1.5 to about 0.5, more preferably from about 1 to about 1, moles of the aromatic compound per mole of the polymer.

The selected acid catalyst can be employed in widely varying concentrations. Generally, the catalyst will be charged to provide at least about 0.001, preferably from about 0.9 to about 2.0, more preferably from 0.05 to 0.4, moles of catalyst per mole of polymer alkylating agent charged to the alkylation reaction zone. Use of greater than 1 mole of the inorganic catalyst per mole of polymer alkylating agent is not generally required.

A useful range of moles catalyst to moles of olefin to moles of hydroxyl aromatic is 0.1-10/0.01/0.1 to 0.1-1/1/1, e.g., 0.1-5/1/0.1-10.

The temperature for alkylation can also vary widely, and will typically range from about 0° C. to about 250° C. The preferred temperature range depends on the type of catalyst used. For most homogeneous or liquid Lewis or Protonic acids, 20° C. to 150° C. will be the preferred range. For solid catalysts, such as ion-exchange resins or solid catalysts, higher reaction temperature is preferred, such as from 40° C. to 250° C.

The alkylation reaction time can vary and will generally be from 0.5 to 5 hours, although longer or shorter times can also be employed. The alkylation process can be practiced in a batchwise, continuous or semicontinuous manner.

The reaction may be carried out with or without a solvent. When no solvent is added, the polymer or the hydroxyaromatic compounds can act as a solvent. The solvents may be polar or non-polar with the proviso that they not be protic. Non-polar solvents are preferred since solvents of high enough polarity, even if non-protic, may cause partial or complete dissolution of the catalyst. Hence, preferred solvents include aliphatic hydrocarbons, halogenated hydrocarbons, etc.

Preferred solvents are those sufficiently less volatile than water, under the reaction conditions utilized, so as to allow water to be driven out of the reaction mixture with minimal loss of solvent. Such solvents include the hydroxyaromatic reactants themselves as well as chlorinated aromatics such as the dichlorobenzenes (ortho, meta, and para), and hydrocarbons such as heptane, decane, and the like. Preferred hydrocarbon solvents may be obtained from ExxonMobil Chemical Company in Houston Tex. under the Tradenames ISOPAR™ and NORPAR™.

For mass production it is preferred that a continuous process be utilized. This involves continuously introducing reactants and solvents into a reaction zone and continuously drawing off the products of the reaction.

While monoalkylated hydroxyaromatics are the primary product discussed in this disclosure, multi-substituted aromatic compositions can also be formed. These alkylated products can be separated from unreacted hydroxyaromatics by distillation, aqueous extraction or any other proper means to separate the light ends from the finished product.

In general any means of separation that will provide a useful liquid hydroxyaromatic functionalized polyalpha-olefin composition is useful.

In another embodiment, the hydroxyaromatic functionalized polyalpha-olefins described herein may be used as plasticizers in polymer blends. The blends preferably comprise from 0.1 wt. % to 70 wt. % (preferably 1 wt. % to 50 wt. %, preferably 5 wt. % to 40 wt. %) of the inventive materials described herein and from 99.9 wt. % to 30 wt. % of one or more polymers. In preferred embodiments the inventive material is a hydroxyaromatic functionalized polyalpha-olefin having a flash point of 200° C. or more (preferably 230° C. or more, preferably 250° C. or more) and a pour point of 0° C. or less (preferably –10° C. or less, preferably –25° C. or less).

Preferred polymers that may blended with the inventive materials of this invention include polyolefins (homopolymers and copolymers of C2 to C20 olefins (preferably ethylene, propylene, butene, hexene, and octene)) such as polyethylene, polypropylene, polybutene, ethylene propylene rubber, ethylene propylene diene monomer rubber, and the like. Useful polyolefins have a weight average molecular weight (GPC, polystyrene standards) of 5,000 to 1,000,000, preferably 50,000 to 500,000. Preferred polymers include plastics, thermoplastics, plastomers and elastomers.

Alternate preferred polymers that may blended with the inventive materials of this invention include polymers of polar monomers, or monomers containing heteroatoms, including but not limited to, polyamides, polyesters, polynitrile resins, ethylene vinyl acetate, polyurethane, polyvinylchloride, and the like. A preferred group of polymers that may be blended with inventive materials herein includes polar polymers, such as engineering resins, particularly those described at page 22, line 26 to page 24, line 5 of WO 2007/050071. Particularly useful engineering resins are thermoplastic polymers, copolymers or mixtures thereof, having a Young's modulus (ASTM D 412-92, room temperature) of more than 500 MPa and, preferably, a melting point (DSC, second melt, 10° C./min) of about 170° C. to about 230° C.

In another embodiment, this invention further relates to:

1. A hydroxyaromatic functionalized polyalpha-olefin comprising the product of the combination of:
   a) a polyalpha-olefin comprising one or more C3 to C20 linear alpha-olefins and having at least 10% vinylidene unsaturation, a viscosity index of 80 to 400, an Mn of 300 to about 20,000, and a pour point of 0° C. or less; and
   b) a hydroxyaromatic moiety;
wherein the analine point of the functionalized polyalpha-olefin is at least 10° C. lower than the analine point of the polyalpha-olefin.

2. The functionalized polyalpha-olefin of paragraph 1 wherein the polyalpha-olefin has a kinematic viscosity of 3 to 1000 cSt.

3. The functionalized polyalpha-olefin of paragraph 1 or 2 where the a polyalpha-olefin has at least 12% vinylidene unsaturation.

4. The functionalized polyalpha-olefin of any of paragraphs 1 to 3 wherein the functionalized polyalpha-olefin has a viscosity index of 80 to 400.

5. The functionalized polyalpha-olefin of any of paragraphs 1 to 4 where the a polyalpha-olefin has a viscosity index within at least 100% of the viscosity index of the polyalpha-olefin.

6. The functionalized polyalpha-olefin of any of paragraphs 1 to 5 wherein the functionalized polyalpha-olefin has a pour point of −5° C. or less.

7. The functionalized polyalpha-olefin of any of paragraphs 1 to 6 wherein the functionalized polyalpha-olefin has an oxidation starting point of at least 40° C. more than the polyalpha-olefin.

8. The functionalized polyalpha-olefin of any of paragraphs 1 to 7, wherein the polyalpha-olefin comprises three or more olefins selected from the group consisting of C5 to C20 alpha-olefins.

9. The functionalized polyalpha-olefin of any of paragraphs 1 to 7, wherein the polyalpha-olefin comprises three or more olefins selected from the group consisting of 1-butene, 1-pentene, 1-hexene, 1-heptene, 1-octene, 1-nonene, 1-decene, 1-undecene, 1-dodecene, 1-tridecene and 1-tetradecene, hexadecene, and octadecene.

10. The functionalized polyalpha-olefin of any of paragraphs 1 to 9, wherein the hydroxyaromatic moiety is chosen from a phenol, a naphthol or a catechol.

11. The functionalized polyalpha-olefin of paragraph 10, wherein the hydroxyaromatic moiety is a phenol.

12. The functionalized polyalpha-olefin of any of paragraphs 1 to 11 wherein the functionalized polyalpha-olefin is at least 90 wt. % monofunctionalized.

13. The functionalized polyalpha-olefin of any of paragraphs 1 to 12 wherein the functionalized polyalpha-olefin contains less than 5% of the vinylidene sites present in the polyalpha-olefin.

14. The functionalized polyalpha-olefin of any of paragraphs 1 to 13 wherein the functionalized polyalpha-olefin has more than 20% of the benzylic carbon atoms present as quaternary carbon atoms.

15. A process for the preparation of a hydroxyaromatic functionalized polyalpha-olefin compound (preferably the functionalized polyalpha-olefin of any of paragraphs 1 to 14) comprising: contacting at least one hydroxyaromatic compound and at least polyalpha-olefin in the presence of an acidic alkylation catalyst under alkylation conditions, wherein the polyalpha-olefin comprises one or more C3 to C20 linear alpha-olefins and has at least 10% vinylidene unsaturation, a viscosity index of 80 to 400, an Mn of 300 to about 20,000, and a pour point of 0° C. or less; and wherein the analine point of the functionalized polyalpha-olefin is at least 10° C. lower than the analine point of the polyalpha-olefin.

16. The process of paragraph 15 further comprising: separating and recovering said hydroxyaromatic functionalized metallocene-derived polyalpha-olefin compound.

17. The process of paragraph 15 or 16 wherein said acidic alkylation catalyst is chosen from halides of boron, aluminum, tin, a transition metal or mixtures thereof.

18. The process of any of paragraphs 15 to 17 wherein the polyalpha-olefin has at least 10% vinylidene unsaturation.

19. The process of any of paragraphs 15 to 18 wherein the residence time is less than 48 hours.

20. A lubricant comprising the functionalized polyalpha-olefin of any of paragraphs 1 to 14.

21. A blend comprising polymer and the functionalized poly-alpha-olefin of any of paragraphs 1 to 14.

22. The blend of claim 14 wherein the polymer comprises a polyolefin (such as homopolymer or copolymer of one or more C2 to C20 olefins), and/or a polar polymer (such as an engineering resin).

EXAMPLES

Fluid properties were measured by following standard methods: kinematic viscosity ($K_v$) at 40 and 100° C. in cSt by ASTM D 445 method; pour point by ASTM D 97 method; and viscosity index (VI) according to ASTM D 2270 method.

The general description of the method to synthesize the molecules can be found in WO 2007/011973, WO 2007/011832, WO 2007/011459. All toluene solvent and feed alpha-olefins were purified according to methods described in these patents. All steps and manipulations were carried out under nitrogen atmosphere to avoid any catalyst deactivation or poison by air, oxygen, moisture and other poisons.

Preparation of stock solutions used in mPAO Synthesis—Triisobutylaluminum (TIBA) or tri-n-octylaluminum (TNOA) stock solution was prepared by dissolving 4 grams of a 25 wt. % TIBA or TNOA in toluene (available from Aldrich Chemical Co.) in 46 gram purified toluene solvent. All metallocene stock solution was prepared by dissolving 0.05 gram metallocene in 49.95 gram purified toluene solvent. Non-coordinating anion (NCA) activator stock solution was prepared by dissolving 0.05 gram N,N-dimethylanilinium tetra(pentafluorophenyl)borate in 49.95 gram purified toluene solvent.

mPAO used in this example was synthesized using a batch mode of operation. This sample was prepared by charging 50 gram purified 1-decene and 3.173 gram of TIBA stock solution into a 500 ml flask under nitrogen atmosphere. The reaction flask was the heated to 120° C. with stirring. A solution in an additional funnel mounted on the reaction flask containing 20 gram toluene, 0.079 gram TIBA stock solution, 0.430 gram stock solution of rac-ethylenebis(4,5,6,7-tetrahydro-1-indenyl)zirconium dichloride and 0.8012 NCA stock solution was added to the 1-decene mixture within 15 minutes while maintaining reaction temperature close to 120° C., no more than 3° C. higher or lower. The reaction mixture was stirred at reaction temperature for 16 hours. Then heat was turn off and quenched with 3 ml isopropanol. The crude product was then washed with 100 ml of a 5% aqueous NaOH solution, followed by 100 ml DI water three times. The organic layer was then separated and dried by 20 gram sodium sulfate for one hour. The solid was filtered. The filtrate was distilled first by low vacuum distillation to remove toluene and unreacted 1-decene, followed by high vacuum distillation at 160° C./1 millitorr vacuum to isolate only C30 and higher oligomers. This oligomer fraction was used for further functionalization reaction.

The alkylation of phenol with olefin terminated poly (decene-1) was carried out as follows.

A two necked 100 mL round bottom flask equipped with a magnetic stirring bar, Reflux condenser, was dried and cooled under argon. 15 mL of dried n-hexane was transferred into the flask by a syringe followed by 1.2893 g (FW 94.11, 0.0137 mol) phenol. 0.2956 g (FW 141.93, 0.00208 moles) of $BF_3.Et_2O$ in 10 mL of hexane was then added to the phenol solution. The mixture was heated to 45° C. 2 g (0.00274 moles of double bonds) of terminally unsaturated PAO with $M_n$ 731 (4.84 mmol of >C=C) was dissolved in 15 mL of n-hexane and was slowly added to the above phenol solution. The mixture was stirred at 50° C. for 24 hours. The solution was cooled to room temperature and was added to 100 mL of water. The organic layer was washed five times with hot water followed by a 50/50 methanol/5% NaOH solution. The organic layer was then washed three times with water followed by 10% HCl followed by three washes with distilled water. The organic layer was then dried over $MgSO_4$ and solvent was removed on the rotary evaporator. Yield 2.18 g.

The product was characterized using IR, NMR and GPC. The FTIR spectra of the starting PAO showed that vinyl double bond peak at 3069, 1643 and 889 $cm^{-1}$. After the phenol alkylation reaction, the double bond peaks disappeared and new peaks at 3615, 3345, 1613 and 1596 appeared. The product was examined by carbon NMR to determine the composition of the copolymer. The sample was prepared in chloroform-d with chromium acetylacetonate, $Cr(acac)_3$, relaxation agent added to the carbon sample to accelerate data acquisition. The spectrum was acquired with the 10 mm broadband probe on the JEOL Delta 400 for 10000 scans at the temperature of 50° C. The $^{13}C$ NMR results suggest that all the vinylidene double bonds are reacted on the phenol alkylation reaction.

A gel permeation chromatography (GPC) trace of the starting PAO and phenol functionalized products were done in THF at 25° C. GPC analysis of the product gave the number average molecular weight of 1092 ($M_n$ 1092) and the weight average molecular weight of 1243 ($M_n$ 1243) using polystyrene standards. GPC analysis of the PAO gave the number average molecular weight of 1062 ($M_n$ 1062) and the weight average molecular weight of 1232 ($M_w$ 1232) using polystyrene standards. A gel permeation chromatography (GPC) trace using the UV detector at 254 nm showed a very large absorption for the phenol reacted polymer suggesting that phenol is attached to the polymer chain. The viscometric and lube properties of the metallocene PAO is shown in Table 1.

Example 2

Phenol Alkylation of Metallocene PAO Synthesized Using Mixed C6-C18 Alpha-Olefins Using Acid Catalyst mPAO used in this example was synthesized in the same manner as the mPAO in Example 1, except 60 gram of a LAO mixture containing 7.1% 1-hexene, 9.5% 1-octene, 11.9% 1-decene, 14.2% 1-dodecene, 16.7% 1-tetradecene, 18.1% 1-hexadecene, 21.4%-octadecene (all in weight %) and 1.044 gram TIBA was charge in reaction flask. The catalyst solution contained 20 gram toluene, 0.0268 gram TIBA stock solution, 0.616 gram stock solution of 70% meso-dimethylsilyl-bis(4,5,6,7tetrahydro-1-indenyl)zirconium dichloride and 30% corresponding rac-isomer, and 1.082 gram NCA stock solution. The reaction temperature was maintained at 31° C. for 16 hours. The reaction was worked up in similar manner. The final oligomer fraction was used for functionalization.

The alkylation of phenol with olefin terminated PAO synthesized using mixed C6-C18 alpha-olefins was carried out as follows.

A two necked 100 mL round bottom flask equipped with a magnetic stirring bar, Reflux condenser, was dried and cooled under argon. 150 mL of dried n-hexane was transferred into the flask by a syringe followed by 12.89 g (FW 94.11, 0.137 mol) phenol. 2.952 g (FW 141.93, 0.0208 moles) of $BF_3.Et_2O$ in 100 mL of hexane was then added to the phenol solution. The mixture was heated to 45° C. 20 g of terminally unsaturated PAO with was dissolved in 50 mL of n-hexane and was added to above phenol solution. The mixture was stirred at 50° C. for 24 hours. The solution was cooled to room temperature and was added to 200 mL of water. The organic layer was washed five times with hot water followed by a 50/50 methanol/5% NaOH solution. The organic layer was then washed three times with water followed by 10% HCl followed by three washes with distilled water. The organic layer was then dried over $MgSO_4$ and solvent was removed on the rotary evaporator. Yield 20 g.

The product was characterized using IR, NMR and GPC. The FTIR spectra of the starting PAO showed that vinyl double bond peak at 3069, 1643 and 889 $cm^{-1}$. On phenol alkylation reaction the double bond peaks disappeared and new peaks at 3615, 3345, 1613 and 1596 appeared. The viscometric and lube properties of the metallocene PAO is shown in Table 1.

TABLE I

| Sample | Pour Point (° C.) | VI | Kinematic Viscosity (100° C., cSt) | Kinematic Viscosity (40° C., cSt) |
|---|---|---|---|---|
| Ex. 1 starting metallocene PAO | −56 | 149 | 8.3 | 45.1 |
| Ex. 1 product of metallocene PAO alkylated with Phenol | −49 | 100 | 9.78 | 74.94 |
| Ex. 2 starting metallocene PAO | −3 | 231 | 93.15 | 723.79 |
| Ex. 2 product of metallocene PAO alkylated with Phenol | −6 | 190 | 104.73 | 1027.64 |

Example 3 (Comparative)

Polyisobutylene Alkylation with Phenol

The alkylation of phenol with polyisobutylene (PIB Indopol H100, Mn~958, commercially available from Inovene) was carried out as follows A two necked 500 mL round bottom flask equipped with a magnetic stirring bar, Reflux condenser, was dried and cooled under argon. 100 mL of dried n-hexane was transferred into the flask by a syringe followed by 6.88 g (FW 94.11, 0.0731 mol) phenol. 5.18 g (FW 141.93, 0.0365 moles) of $BF_3.Et_2O$ in 10 mL of hexane was then added to the phenol solution. The mixture was heated to 45° C. 35 g (0.0365 moles of double bonds) of polyisobutylene with an $M_n$ of 958 was dissolved in 15 mL of n-hexane and was slowly added to the above phenol solution. The mixture was stirred at 50° C. for 24 hours. The solution was cooled to room temperature and was added to 100 mL of water. The organic layer was washed five times with hot water followed by a 50/50 methanol/5% NaOH solution. The organic layer was then washed three times with water followed by 10% HCl followed by three washes with distilled water. The organic layer was then dried over $MgSO_4$ and solvent was removed on the rotary evaporator. Yield 37.2 g.

The product was characterized using NMR and GPC. The product was examined by carbon NMR to determine the composition of the copolymer. The sample was prepared in chloroform-d with chromium acetylacetonate, $Cr(acac)_3$, relaxation agent added to the carbon sample to accelerate data acquisition. The spectrum was acquired with the 10 mm broadband probe on the JEOL Delta 400 for 10000 scans at the temperature of 50° C. The $^{13}C$ NMR results suggest that 67% double bonds are reacted on the phenol alkylation reaction. (acac=acetylacetonate)

A gel permeation chromatography (GPC) trace of the starting PIB and phenol functionalized products were done in THF at 25° C. GPC analysis of the product gave the number average molecular weight of 953 ($M_n$ 953) and the weight average molecular weight of 2046 ($M_w$ 2046) using polystyrene standards. The GPC trace using the UV detector at 254 nm showed a very large absorption for the phenol reacted polymer suggesting that phenol is attached to the polymer.

The viscosity of phenol reacted PIB gave Kv at 100° C. of 94.72 cSt, Kv at 40° C. of 4937.24 cSt with VI of 50.

Example 4

Commercial PAO Alkylation with Phenol

The alkylation of phenol with PAO (6 cSt commercial PAO, Mn~850): This sample was produced from C8 to C12 linear alpha-olefins using promoted $BF_3$ catalyst. The resulting PAO was isolated by fractionation to remove solvent, light ends or any unreacted starting material. This PAO had a bromine number about 30.

A two necked 500 mL round bottom flask equipped with a magnetic stirring bar, Reflux condenser, was dried and cooled under argon. 100 mL of dried n-hexane was transferred into the flask by a syringe followed by 7.75 g (FW 94.11, 0.0824 mol) phenol. 5.85 g (FW 141.93, 0.0412 mol) of $BF_3.Et_2O$ in 10 mL of hexane was then added to the phenol solution. The mixture was heated to 45° C. 35 g (0.0412 moles of double bonds) of unsaturated PAO with $M_n$ 850 and $KV_{100}$ of 6 cSt was dissolved in 15 mL of n-hexane and was slowly added to the above phenol solution. The mixture was stirred at 50° C. for 24 hours. The solution was cooled to room temperature and was added to 100 mL of water. The organic layer was washed five times with hot water followed by a 50/50 methanol/5% NaOH solution. The organic layer was then washed three times with water followed by 10% HCl followed by three washes with distilled water. The organic layer was then dried over $MgSO_4$ and solvent was removed on the rotary evaporator. Yield 36.1 g.

The product was characterized using NMR and GPC. The product was examined by carbon NMR to determine the composition of the copolymer. The sample was prepared in chloroform-d with chromium acetylacetonate, $Cr(acac)_3$, relaxation agent added to the carbon sample to accelerate data acquisition. The spectrum was acquired with the 10 mm broadband probe on the JEOL Delta 400 for 10000 scans at the temperature of 50° C. The $^{13}C$ NMR results suggest that 14% double bonds are reacted on the phenol alkylation reaction.

A gel permeation chromatography (GPC) trace of the starting phenol functionalized products was done in THF at 25° C. GPC analysis of the product gave the number average molecular weight of 870 ($M_n$ 870) and the weight average molecular weight of 924 ($M_w$ 924) using polystyrene standards. GPC analysis of the PAO gave the number average molecular weight of 850 ($M_n$ 850) and the weight average molecular weight of 901 ($M_w$ 901) using polystyrene standards. The GPC trace using the UV detector at 254 nm showed a very large absorption for the phenol reacted polymer suggesting that phenol is attached to the polymer.

The viscosity of phenol reacted PAO gave Kv at 100° C. of 5.38 cSt, Kv at 40° C. of 26.67 cSt with VI of 129.

Example 5

Metallocene PAO Alkylation with Phenol mPAO used in this example was synthesized similar as the mPAO in Example 1, except the reaction was conducted in a 600-ml Parr autoclave. In this run, 90 grams 1-decene and 4.0 grams of TNOAL stock solution was charged into the autoclave and heated to 80° C. The reactor was pressurized with 10 psi of hydrogen pressure. Then, a catalyst solution containing 20 gram toluene and 0.5 gram TNOAL stock solution, 1.60 gram stock solution of bis(1-methyl-3-n-butylcyclopentadienyl)zirconium dimethyl and 3.84 gram of NCA activator were charge into the autoclave. After 16 hours of reaction, the reactor was cooled down, vented and then work up in the similar manner as in Example 3. The resulting PAO had the following properties: 100° C. Kv=10.11 cS, 40° C. Kv=56.67 cS, VI=156. Mn by GPC=1080. Typically, this type of metallocene derived PAO has 4% 1,2-disubstituted olefin, 19% tri-substituted olefin and 77% vinylidene olefin by either H1-NMR or C13-NMR. The alkylation of phenol with this PAO was carried out as follows:

A two necked 500 mL round bottom flask equipped with a magnetic stirring bar, Reflux condenser, was dried and cooled under argon. 100 mL of dried n-hexane was transferred into the flask by a syringe followed by 6.09 g (FW 94.11, 0.0648 mol) phenol. 4.60 g (FW 141.93, 0.0324 mol) of $BF_3.Et_2O$ in 10 mL of hexane was then added to the phenol solution. The mixture was heated to 45° C. 35 g the unsaturated PAO was dissolved in 15 mL of n-hexane and was slowly added to the above phenol solution. The mixture was stirred at 50° C. for 24 hours. The solution was cooled to room temperature and was added to 100 mL of water. The organic layer was washed five times with hot water followed by a 50/50 methanol/5% NaOH solution. The organic layer was then washed three times with water followed by 10% HCl followed by three washes with distilled water. The organic layer was then dried over $MgSO_4$ and solvent was removed on the rotary evaporator. Yield 37.1 g.

The product was characterized using NMR and GPC. The product was examined by carbon NMR to determine the composition of the copolymer. The sample was prepared in chloroform-d with chromium acetylacetonate, $Cr(acac)_3$, relaxation agent added to the carbon sample to accelerate data acquisition. The spectrum was acquired with the 10 mm broadband probe on the JEOL Delta 400 for 10000 scans at the temperature of 50° C. The $^{13}$C NMR results suggest that 54% double bonds are reacted on the phenol alkylation reaction.

A gel permeation chromatography (GPC) trace of the starting phenol functionalized products was done in THF at 25° C. GPC analysis of the product gave the number average molecular weight of 1174 ($M_n$ 1174) and the weight average molecular weight of 1538 ($M_w$ 1538) using polystyrene standards. The GPC trace using the UV detector at 254 nm showed a very large absorption for the phenol reacted polymer suggesting that phenol is attached to the polymer.

The viscosity of phenol reacted PAO gave Kv at 100° C. of 11.97 cSt, Kv at 40° C. of 88.23 cSt with VI of 118.

Example 6

Conventional PAO Alkylation with Phenol

The alkylation of phenol with conventional PAO: This conventional PAO sample was produced from C8 to C12 linear alpha-olefins using promoted AlCl3 catalyst. The resulting PAO was isolated by fractionation to remove solvent, light ends or any unreacted starting material. This PAO typically has a 100° C. Kv of 30-40 cS, 40° C. Kv of 350-440 cS and VI of 135 to 145 and bromine number about 10-13.

The phenol alkylation of this unsaturated PAO was carried out as follows:

A two necked 500 mL round bottom flask equipped with a magnetic stirring bar, Reflux condenser, was dried and cooled under argon. 100 mL of dried n-hexane was transferred into the flask by a syringe followed by 5.49 g (FW 94.11, 0.0583 mol) phenol. 4.14 g (FW 141.93, 0.0292 mol) of BF$_3$.Et$_2$O in 10 mL of hexane was then added to the phenol solution. The mixture was heated to 45° C. 35 g (0.0292 moles of double bonds) of unsaturated PAO with $M_n$ 1200 was dissolved in 15 mL of n-hexane and was slowly added to the above phenol solution. The mixture was stirred at 50° C. for 24 hours. The solution was cooled to room temperature and was added to 100 mL of water. The organic layer was washed five times with hot water followed by a 50/50 methanol/5% NaOH solution. The organic layer was then washed three times with water followed by 10% HCl followed by three washes with distilled water. The organic layer was then dried over MgSO$_4$ and solvent was removed on the rotary evaporator. Yield 34.3 g.

The product was characterized using NMR and GPC. The product was examined by carbon NMR to determine the composition of the copolymer. The sample was prepared in chloroform-d with chromium acetylacetonate, Cr(acac)$_3$, relaxation agent added to the carbon sample to accelerate data acquisition. The spectrum was acquired with the 10 mm broadband probe on the JEOL Delta 400 for 10000 scans at the temperature of 50° C. The $^{13}$C NMR results suggest that 4% double bonds are reacted on the phenol alkylation reaction.

The viscosity of phenol reacted PAO gave Kv at 100° C. of 34.08 cSt, Kv at 40° C. of 287.37 cSt with VI of 155.

Table II reports data which demonstrates that metallocene based PAO's react differently than non-metallocene derived PAO's. The percentage of available double bonds alkylated in metallocene based PAO's is significantly increased over that of non-metallocene based PAO's.

TABLE II

|  | Ex 3 Starting PIB PIB H100 | Ex. 3 Product PIB-phenol | Ex 4 Starting conventional PAO PAO 6 cS | Ex. 4 Product PAO-phenol | Ex. 5 Starting metallocene PAO mPAO | Ex. 5 Product mPAO-phenol | Ex. 6 Starting conventional PAO PAO 40 cS | Ex. 6 Product PAO-phenol |
|---|---|---|---|---|---|---|---|---|
| Kv 100 cSt | 218 | 94.72 | 5.8 | 5.38 |  | 11.97 | 39 | 34.08 |
| Kv 40 cSt |  | 4937.24 | 31 | 26.67 |  | 88.23 | 396 | 287.37 |
| VI | 121 | 50 | 138 | 129 |  | 118 | 147 | 155 |
| % react 1 H NMR |  | 73 |  | 18 |  | 56 |  | 17 |
| % react 13C NMR |  | 67 |  | 14 |  | 54 |  | 4 |
| Average Conversion (Wt. %) |  | 70 |  | 16 |  | 55 |  | 10 |
| DSC Induction Temperature (° C.) | 184 | 236 | 181 | 214 | 188 | 251 | 190 | 214 |
| Pour Point (° C.) | −7 |  | −57 |  |  |  | −36 |  |
| Mn | 958 |  | 850 |  | 1080 |  | 1200 |  |

Oxidation Starting Temperature by DSC(10° C. per minute heating rate).

All patents, test procedures, and other documents cited herein, including priority documents, are fully incorporated by reference to the extent such disclosure is not inconsistent with this disclosure and for all jurisdictions in which such incorporation is permitted. When numerical lower limits and numerical upper limits are listed herein, ranges from any lower limit to any upper limit are contemplated.

What is claimed is:

1. A hydroxyaromatic functionalized polyalpha-olefin comprising the product of the combination of:
   a) a polyalpha-olefin having 0 wt % isobutylene and comprising one or more C3 to C20 linear alpha-olefins selected from the group consisting of 1-decene, 1-undecene, 1-dodecene, 1-tridecene and 1-tetradecene, and having at least 10% vinylidene unsaturation, a viscosity index of 80 to 400, an Mn of 300 to about 20,000, and a pour point of 0° C. or less; and b) a hydroxyaromatic moiety;
wherein the aniline point of the functionalized polyalpha-olefin is at least 10° C. lower than the aniline point of the polyalpha-olefin, and wherein the oxidation induction temperature is 225° C. or more; and
wherein the functionalized polyalpha-olefin has more than 20% of the benzylic carbon atoms present as quaternary carbon atoms.

2. The functionalized polyalpha-olefin of claim 1 wherein the polyalpha-olefin has a kinematic viscosity of 3 to 1000 cSt.

3. The functionalized polyalpha-olefin of claim 1 wherein the polyalpha-olefin has at least 12% vinylidene unsaturation.

4. The functionalized polyalpha-olefin of claim 1 wherein the functionalized polyalpha-olefin has a viscosity index of 80 to 400.

5. The functionalized polyalpha-olefin of claim 1 wherein the functionalized polyalpha-olefin has a pour point of −5° C. or less.

6. The functionalized polyalpha-olefin of claim 1 wherein the functionalized polyalpha-olefin has an oxidation starting point of at least 40° C. more than the polyalpha-olefin.

7. The functionalized polyalpha-olefin of claim 1, wherein the polyalpha-olefin comprises three or more olefins selected from the group consisting of C5 to C20 alpha-olefins.

8. The functionalized polyalpha-olefin of claim 1, wherein the polyalpha-olefin comprises three or more olefins selected from the group consisting of 1-butene, 1-pentene, 1-hexene, 1-heptene, 1-octene, 1-nonene, 1-decene, 1-undecene, 1-dodecene, 1-tridecene, 1-tetradecene, hexadecene, and octadecene.

9. The functionalized polyalpha-olefin of claim 1, wherein the hydroxyaromatic moiety is chosen from a phenol, a naphthol or a catechol.

10. The functionalized polyalpha-olefin of claim 1, wherein the hydroxyaromatic moiety is a phenol.

11. The functionalized polyalpha-olefin of claim 1 wherein the functionalized polyalpha-olefin is at least 90 wt. % monofunctionalized.

12. The functionalized polyalpha-olefin of claim 1 wherein the functionalized polyalpha-olefin contains less than 5% of the vinylidene sites present in the polyalpha-olefin.

13. A lubricant comprising the functionalized polyalpha-olefin of claim 1.

14. A blend comprising polymer and the functionalized polyalpha-olefin of claim 1.

15. The blend of claim 14 wherein the polymer comprises a polyolefin.

16. The blend of claim 14 wherein the polymer comprises a polar polymer.

17. The blend of claim 14 wherein the polymer is a homopolymer or copolymer of one or more C2 to C20 olefins.

18. The blend of claim 14 wherein the polymer comprises an engineering resin.

19. The functionalized polyalpha-olefin of claim 1 wherein the polyalpha-olefin has a viscosity of 20 to 5000 cSt and a Bromine number of from 25 to less than 1.

20. The functionalized polyalpha-olefin of claim 1 wherein the polyalpha-olefin has a viscosity index of 100 to 300.

21. The functionalized polyalpha-olefin of claim 1, wherein the hydroxyaromatic moiety is selected from the group consisting of phenol, o-, m-, or p-cresol, o-, m-, or p-ethylphenol, o-, m-, or p-isopropylphenol, o-, m-, or p-tert-butylphenol, o-, m-, or p-sec-butylphenol, 4-tert-butyl-6-methylphenol, 2,4-dimethylphenol, 2-methyl-4-ethylphenol, 2,4-diisopropylphenol, 4-methyl-6-iso-propylphenol, 2,6-di-tert-butylphenol, 2-tert-butyl-4-methylphenol, 3-methyl-6-tert-butylphenol, 2-chloro-4-methylphenol, p-chlorophenol, p-bromophenol, 2,4-dichlorophenol, 2,4-dibromophenol, 2-methyl-4-chloro-phenol, 2-methyl-4-bromophenol, 2,4-dichloro-3-methylphenol, 3-methyl-6-cyclohexylphenol, 3-methyl-4-cyclohexylphenol, resorcinol, hydroquinone, catechol, 2-methylresorcinol, 2-chlororesorcinol, 2-carboxyresorcinol, 2-chlorohydroquinone, 4-tert-butylresorcinol, pyrogallol, phloroglucinol, 1,2,4-trihydroxybenzene, gallic acid, alpha-naphthol, beta-naphthol, 2-hydroxy-3-carboxy naphthalene, 1-hydroxy-5-methyl naphthalene, 2-hydroxy-5-methyl naphthalene, 2-hydroxy-8-isopropyl-naphthalene, 2-hydroxy-5-isopropyl naphthalene, and anthranols.

22. The functionalized polyalpha-olefin of claim 1, wherein the hydroxyaromatic moiety has at least one aromatic ring bound to a hydroxyl group and has at least one open carbon at a position ortho or para thereto.

23. The functionalized polyalpha-olefin of claim 1 wherein the oxidation induction temperature is 245° C. or more.

24. The functionalized polyalpha-olefin of claim 1, formed from contacting a molar ratio of hydroxyaromatic compound to polyalpha-olefin of from 1.5:0.5 to 1:1.

25. The functionalized polyalpha-olefin of claim 1, wherein the polyalpha-olefin is produced by metallocene catalyzed polymerization.

26. A hydroxyaromatic functionalized polyalpha-olefin comprising the product of the combination of:
a) a polyalpha-olefin containing 0 wt % isobutylene and comprising two or more olefins selected from the group consisting of 1-decene, 1-undecene, 1-dodecene, 1-tridecene, 1-tetradecene, and having at least 10% vinylidene unsaturation, a viscosity index of 80 to 400, an Mn of 300 to about 20,000, an aniline point of 110° C. to 170° C., and a pour point of 0° C. or less; and
b) a hydroxyaromatic moiety;
wherein the aniline point of the functionalized polyalpha-olefin is at least 10° C. lower than the aniline point of the polyalpha-olefin, and wherein the oxidation induction temperature is 225° C. or more; and
wherein the functionalized polyalpha-olefin has more than 20% of the benzylic carbon atoms present as quaternary carbon atoms.

27. The functionalized polyalpha-olefin of claim 26 wherein the oxidation induction temperature is 245° C. or more.

28. A hydroxyaromatic functionalized polyalpha-olefin comprising the product of the combination of:
a) a polyalpha-olefin containing 0 wt % isobutylene and comprising three or more olefins selected from the group consisting of 1-hexene, 1-heptene, 1-octene, 1-nonene, 1-decene, 1-undecene, 1-dodecene, 1-tridecene, 1-tetradecene, hexadecene, and octadecene, and having at least 10% vinylidene unsaturation, a viscosity index of 80 to 400, an Mn of 300 to about 20,000, an aniline point of 110° C. to 170° C., and a pour point of 0° C. or less; and
b) a hydroxyaromatic moiety;
wherein the aniline point of the functionalized polyalpha-olefin is at least 10° C. lower than the aniline point of the polyalpha-olefin, and wherein the oxidation induction temperature is 225° C. or more; and
wherein the functionalized polyalpha-olefin has more than 20% of the benzylic carbon atoms present as quaternary carbon atoms.

29. The functionalized polyalpha-olefin of claim 28 wherein the oxidation induction temperature is 245° C. or more.

30. A hydroxyaromatic functionalized polyalpha-olefin comprising the product of the combination of:
  a) a polyalpha-olefin containing 0 wt % isobutylene and comprising 1-octene, 1-decene, 1-dodecene, and having at least 10% vinylidene unsaturation, a viscosity index of 80 to 400, an Mn of 300 to about 20,000, an aniline point of 110° C. to 170° C., and a pour point of 0° C. or less; and
  b) a hydroxyaromatic moiety;
  wherein the aniline point of the functionalized polyalpha-olefin is at least 10° C. lower than the aniline point of the polyalpha-olefin, and wherein the oxidation induction temperature is 225° C. or more; and
  wherein the functionalized polyalpha-olefin has more than 20% of the benzylic carbon atoms present as quaternary carbon atoms.

31. The functionalized polyolefin of claim 30 wherein the a polyalpha-olefin consists essentially of 1-octene, 1-decene, 1-dodecene.

32. The functionalized polyalpha-olefin of claim 30 wherein the oxidation induction temperature is 245° C. or more.

33. A hydroxyaromatic functionalized polyalpha-olefin comprising the product of the combination of:
  a) a polyalpha-olefin containing 0 wt % isobutylene and comprising four or more olefins selected from the group consisting of 1-hexene, 1-heptene, 1-octene, 1-nonene, 1-decene, 1-undecene, 1-dodecene, 1-tridecene, 1-tetradecene, hexadecene, and octadecene, and having at least 10% vinylidene unsaturation, a viscosity index of 80 to 400, an Mn of 300 to about 20,000, an aniline point of 110° C. to 170° C., and a pour point of 0° C. or less; and
  b) a hydroxyaromatic moiety;
  wherein the aniline point of the functionalized polyalpha-olefin is at least 10° C. lower than the aniline point of the polyalpha-olefin, and wherein the oxidation induction temperature is 225° C. or more; and
  wherein the functionalized polyalpha-olefin has more than 20% of the benzylic carbon atoms present as quaternary carbon atoms.

34. A hydroxyaromatic functionalized polyalpha-olefin comprising the product of the combination of:
  a) a polyalpha-olefin containing 0 wt % isobutylene and comprising five or more olefins selected from the group consisting of 1-hexene, 1-heptene, 1-octene, 1-nonene, 1-decene, 1-undecene, 1-dodecene, 1-tridecene, 1-tetradecene, hexadecene, and octadecene, and having at least 10% vinylidene unsaturation, a viscosity index of 80 to 400, an Mn of 300 to about 20,000, an aniline point of 110° C. to 170° C., and a pour point of 0° C. or less; and
  b) a hydroxyaromatic moiety;
  wherein the aniline point of the functionalized polyalpha-olefin is at least 10° C. lower than the aniline point of the polyalpha-olefin, and wherein the oxidation induction temperature is 225° C. or more; and
  wherein the functionalized polyalpha-olefin has more than 20% of the benzylic carbon atoms present as quaternary carbon atoms.

35. The functionalized polyalpha-olefin of claim 34, wherein the polyalpha-olefin is produced by metallocene catalyzed polymerization.

36. A hydroxyaromatic functionalized polyalpha-olefin comprising the product of the combination of:
  a) a polyalpha-olefin containing 0 wt % isobutylene and comprising six or more olefins selected from the group consisting of 1-hexene, 1-heptene, 1-octene, 1-nonene, 1-decene, 1-undecene, 1-dodecene, 1-tridecene, 1-tetradecene, hexadecene, and octadecene, and having at least 10% vinylidene unsaturation, a viscosity index of 80 to 400, an Mn of 300 to about 20,000, an aniline point of 110° C. to 170° C., and a pour point of 0° C. or less; and
  b) a hydroxyaromatic moiety;
  wherein the aniline point of the functionalized polyalpha-olefin is at least 10° C. lower than the aniline point of the polyalpha-olefin, and wherein the oxidation induction temperature is 225° C. or more; and
  wherein the functionalized polyalpha-olefin has more than 20% of the benzylic carbon atoms present as quaternary carbon atoms.

37. The functionalized polyalpha-olefin of claim 36, wherein the polyalpha-olefin is produced by metallocene catalyzed polymerization.

* * * * *